(12) United States Patent
Lee et al.

(10) Patent No.: US 8,324,363 B2
(45) Date of Patent: Dec. 4, 2012

(54) MICROARRAY FOR DETECTION OF THE DELETION OF EXON 3 OF THE G-CSF GENE

(76) Inventors: Sang Yup Lee, Daejeon (KR); Nae Choon Yoo, Seoul (KR); So Young Yoo, Seoul (KR); Hyun Cheol Chung, Seoul (KR); Ki Chang Keum, Seoul (KR); Won Min Yoo, Seoul (KR); Ki Jun Jeong, Daejeon (KR)

( * ) Notice: Subject to any disclaimer, the term of this patent is extended or adjusted under 35 U.S.C. 154(b) by 37 days.

(21) Appl. No.: 11/058,976

(22) Filed: Feb. 16, 2005

(65) Prior Publication Data

US 2005/0244856 A1 Nov. 3, 2005

Related U.S. Application Data

(62) Division of application No. 10/490,502, filed as application No. PCT/KR02/01825 on Jan. 18, 2002, now abandoned.

(30) Foreign Application Priority Data

Sep. 28, 2001 (KR) .............................. 2001-0060826

(51) Int. Cl.
*C07H 21/04* (2006.01)
*C12Q 1/68* (2006.01)
*C07K 14/535* (2006.01)

(52) U.S. Cl. ................... 536/24.31; 435/6.12; 435/6.14; 530/350; 930/145

(58) Field of Classification Search .................. None
See application file for complete search history.

(56) References Cited

U.S. PATENT DOCUMENTS 6,303,301 B1 * 10/2001 Mack .................... 435/6

OTHER PUBLICATIONS

Kobaek-Larsen et al, 2000. Comp Med. 50(1): 16-26.*
Rihn et al, 1995 (J. Biochem Biophys Methods, 30: 91-102).*
Deschaseaux et al., "The Detection of colony-stimulating factors and steel factor in adherent layers of human long-term marrow cultures using reverse-transcriptase polymerase chain reaction", Leukemia, vol. 8, No. 3, pp. 513-519 (1994)—Abstract only.
Sauer et al., "A novel procedure for efficient genotyping of single nucleotide polymorphisms", Nucleic Acids Research, vol. 28, No. 5, pp. i-viii (2000).
Brinkman, "Splice variants as cancer biomarkers", Clinical Biochemistry, vol. 37, pp. 584-594 (2004).
Lacroix and Leclercq, "Relevance of breast cancer cell lines as models for breast tumours: an update", Breast Cancer Research and Treatment, vol. 83, pp. 249-289 (2004).
Sorg et al., "Rapid and Sensitive mRNA Phenotyping for Interleukins (IL-1 to IL-6) and Colony-stimulating Factors (G-CSF, M-CSF, and GM-CSF) by Reverse Transcription and Subsequent Polymerase Chain Reaction", Experimental Hematology, vol. 19, pp. 882-887 (1991).

* cited by examiner

*Primary Examiner* — Zachary Howard
(74) *Attorney, Agent, or Firm* — Joseph Hyosuk Kim; JHK Law

(57) ABSTRACT

Disclosed are a method, a composition, a microarray, an antibody and a kit for diagnosis and prognosis of cancer, based on detection of deletion of the exon 3 region of G-CSF gene or levels of a mutated G-CSF protein having a deletion of an amino acid sequence corresponding to the exon 3 region, wherein the deletion of the exon 3 region of the G-CSF gene is used as a cancer biomarker.

4 Claims, 16 Drawing Sheets

SEQUENCE LISTING

```
<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1 accccctgg gccctgcc                                                    18

<210> SEQ ID NO 2
<211> LENGTH: 18
<212> TYPE: DNA
<213> ORGANISM: Artificial Sequence
<220> FEATURE:
<223> OTHER INFORMATION: primer

<400> SEQUENCE: 2
tcagggctgg gcaaggtg                                                   18

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
atccagggcg atggcgcagc g                                               21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
tgtgccacct acaagctgtg c                                               21

<210> SEQ ID NO 5
<211> LENGTH: 18
<212> TYPE: DNA
<213> ORGANISM: Artificial Sequence
<220> FEATURE:
<223> OTHER INFORMATION: primer
```

```
<400> SEQUENCE: 5
cagctgcagg gcctggct                                                 18

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
cgctatggag ttggctcaag c                                             21

<210> SEQ ID NO 7
<211> LENGTH: 525
<212> TYPE: DNA
<213> ORGANISM: Homo sapiens
<220> FEATURE:
<221> NAME/KEY: gene
<222> LOCATION: (1)..(523)
<223> OTHER INFORMATION: G-CSF

<400> SEQUENCE: 7
acccccctgg gccctgccag ctccctgccc cagagcttcc tgctcaagtg cttagagcaa    60
gtgaggaaga tccagggcga tggcgcagcg ctccaggaga agctgtgtgc cacctacaag   120
ctgtgccacc ccgaggagct ggtgctgctc ggacactctc tgggcatccc ctgggctccc   180
ctgagcagct gccccagcca ggccctgcag ctggcaggct gcttgagcca actccatagc   240 ggcctttttcc tctaccaggg gctcctgcag gccctggaag ggatctcccc cgagttgggt   300
cccaccttgg acacactgca gctggacgtc gccgactttg ccaccaccat ctggcagcag   360
atggaagaac tgggaatggc ccctgccctg cagcccaccc agggtgccat gccggccttc   420
gcctctgctt tccagcgccg ggcaggaggg gtcctagttg cctcccatct gcagagcttc   480
ctggaggtgt cgtaccgcgt tctacgccac cttgcccagc cctga                  525

<210> SEQ ID NO 8
<211> LENGTH: 417
<212> TYPE: DNA
<213> ORGANISM: Homo sapiens
<220> FEATURE:
<221> NAME/KEY: gene
<222> LOCATION: (1)..(417)
<223> OTHER INFORMATION: exon 3 deletion G-CSF

<400> SEQUENCE: 8
acccccctgg gccctgccag ctccctgccc cagagcttcc tgctcaagtg cttagagcaa    60
gtgaggaaga tccagggcga tggcgcagcg ctccaggaga agctggcagg ctgcttgagc   120
caactccata gcggcctttt cctctaccag gggctcctgc aggccctgga agggatctcc   180
cccgagttgg gtcccacctt ggacacactg cagctggacg tcgccgactt tgccaccacc   240
atctggcagc agatggaaga actgggaatg gcccctgccc tgcagcccac ccagggtgcc   300
atgccggcct tcgcctctgc tttccagcgc cgggcaggag gggtcctagt tgcctcccat   360
ctgcagagct cctggaggt gtcgtaccgc gttctacgcc accttgccca gccctga       417

<210> SEQ ID NO 9
<211> LENGTH: 18
<212> TYPE: DNA
<213> ORGANISM: Artificial Sequence
<220> FEATURE:
<223> OTHER INFORMATION: primer
```

```
<400> SEQUENCE: 9
cagcttctcc tggagcgc                                                  18

<210> SEQ ID NO 10
<211> LENGTH: 21
<212> TYPE: DNA
<213> ORGANISM: Artificial Sequence
<220> FEATURE:
<223> OTHER INFORMATION: primer and probe

<400> SEQUENCE: 10
ctgcagctgc tgctgtggca c                                              21

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
ctgctgccag atggtggt                                                  18

<210> SEQ ID NO 12
<211> LENGTH: 17
<212> TYPE: DNA
<213> ORGANISM: Artificial Sequence
<220> FEATURE:
<223> OTHER INFORMATION: probe

<400> SEQUENCE: 12
agaagctgtg gtgccac                                                   17

<210> SEQ ID NO 13
<211> LENGTH: 16
<212> TYPE: DNA
<213> ORGANISM: Artificial Sequence
<220> FEATURE:
<223> OTHER INFORMATION: probe

<400> SEQUENCE: 13
tgagtgagtg tgccac                                                    16

<210> SEQ ID NO 14
<211> LENGTH: 20
<212> TYPE: DNA
<213> ORGANISM: Artificial Sequence
<220> FEATURE:
<223> OTHER INFORMATION: probe

<400> SEQUENCE: 14
tgtgccacct acaagctgtg                                                20

<210> SEQ ID NO 15
<211> LENGTH: 20
<212> TYPE: DNA
<213> ORGANISM: Artificial Sequence
<220> FEATURE:
<223> OTHER INFORMATION: probe

<400> SEQUENCE: 15
gagctggtgc tgctcggaca                                                20

<210> SEQ ID NO 16
<211> LENGTH: 20
<212> TYPE: DNA
```

```
<213> ORGANISM: Artificial Sequence
<220> FEATURE:
<223> OTHER INFORMATION: probe

<400> SEQUENCE: 16
ggacactctc tgggcatccc                                          20

<210> SEQ ID NO 17
<211> LENGTH: 20
<212> TYPE: DNA
<213> ORGANISM: Artificial Sequence
<220> FEATURE:
<223> OTHER INFORMATION: probe

<400> SEQUENCE: 17
ctgagcagct gccccagcca                                          20

<210> SEQ ID NO 18
<211> LENGTH: 18
<212> TYPE: DNA
<213> ORGANISM: Artificial Sequence
<220> FEATURE:
<223> OTHER INFORMATION: probe

<400> SEQUENCE: 18
gcaggctgct tgagccaa                                            18

<210> SEQ ID NO 19
<211> LENGTH: 16
<212> TYPE: DNA
<213> ORGANISM: Artificial Sequence
<220> FEATURE:
<223> OTHER INFORMATION: probe

<400> SEQUENCE: 19
agaagctggc aggctg                                              16

<210> SEQ ID NO 20
<211> LENGTH: 16
<212> TYPE: DNA
<213> ORGANISM: Artificial Sequence
<220> FEATURE:
<223> OTHER INFORMATION: probe

<400> SEQUENCE: 20
tgagtgaggc aggctg                                              16
```

MICROARRAY FOR DETECTION OF THE DELETION OF EXON 3 OF THE G-CSF GENE

CONTINUING DATA

The present application is a divisional application of Ser. No. 10/490,502, filed Mar. 22, 2004, and now abandoned, under 35 U.S.C. 371 as a national phase application of PCT/KR02/01825, filed Jan. 18, 2002.

TECHNICAL FIELD

The present invention relates to a method of diagnosing cancer based on modified features in granulocyte colony stimulating factor (G-CSF) mRNA or protein. More particularly, the present invention relates to a diagnostic and prognostic method for cancer based on skipping of the exon 3 region of the G-CSF gene at mRNA or protein levels, wherein skipping of G-CSF exon 3 is used as a diagnostic cancer marker.

PRIOR ART

Cancer is a leading cause of death in developed nations. For this reason, a major interest in cancer therapy is to develop methods for early diagnosis and treatment of cancer. Typically, late-stage cancer is almost incurable, whereas, at the early stage, cancer can be more effectively treated and therapeutic methods for early-stage cancer are simpler. Therefore, there is an urgent need for development of methods for accurately and quickly diagnosing cancer.

At present, cancer diagnosis is generally achieved by morphological analysis using microscopes such as an optical microscope or electron microscope, immunohistochemical assays which detect proteins specifically expressed in cancer tissues (*Iran. Biomed. J.* 3 (3 & 4): 99-101, 1999; and *Lancet* 2:483-6, 1986), or molecular analysis of abnormal biomolecules found in cancer tissues, such as mutated genes. In comparison with the molecular diagnosis, the morphological and immunohistochemical diagnosis requires much longer time and higher cost. Because of comprising a relatively simple procedure and yielding results in a short time, the molecular diagnosis methods are a focus for developing novel diagnostic methods for cancer. Recently, a protein chip system for diagnosing various cancers has been developed by Health Digit Inc. in Shanghai, China, and gained approval for clinical tests from the Chinese State Drug Administration (CSDA). Such an approval is the first in the world (as described at the following worldwide web address: healthdigit.com). However, the protein chip system does not use only a biomarker to diagnose all kinds of cancer, but uses 10 or more proteins.

To effectively apply such diagnostic methods to cancer diagnosis, it is most important to select cancer diagnostic markers capable of more accurately and easily discovering incidence of cancer. As diagnostic cancer markers, several genes (Steve M. et al., J. Clin. Oncology 20:3165-3175, 2002; and Sridihar R et al, J. Clin. Oncology 20:1932-1941, 2002) and proteins (Goessl et al., Urology 58:335-338, 2001; Zhou et al., Breast Cancer Res Treat 66:217-224, 2001; and C K Kim et al., Korea Pat. Publication No. 2001-0061173) have been reported, and some of them are being clinically used for diagnosis of cancer. The conventional cancer biomarkers are unable to detect all kinds of cancer, as follows. The known cancer biomarkers which have low organ specificity, such as CEA, BFP, TPA and IAP, also, have low sensitivity, thus generating false positive data Also, the biomarkers which have high organ specificity, exemplified by AFP, PIVKA II, Esterase I, CA19-9, CA50, Span-1 antigen, CA15-3 and BCA 225, are useful only for target organs. Therefore, for accurate, economical and simple diagnosis of cancer, there is an urgent need for development of new markers capable of diagnosing a variety of cancers.

DISCLOSURE OF THE INVENTION

Leading to the present invention, the thorough and intensive research into a cancer biomarker capable of diagnosing a variety of cancers, conducted by the present inventors, resulted in the finding that exon 3 skipping occurs during transcription of the G-CSF gene in cancer patients, and use of G-CSF mRNA fragment or protein as a diagnostic cancer marker can achieve diagnosis of a variety of cancer, wherein the diagnosis is performed simply and quickly, as well as being economical.

In an aspect of the present invention, there is provided a mutated G-CSF mRNA fragment having a deletion of an exon 3 region for use as a diagnostic cancer marker.

In another aspect of the present invention, there is provided a mutated G-CSF protein having a deletion of an amino acid sequence corresponding to an exon 3 region for use as a cancer diagnostic marker.

In a further aspect of the present invention, there is provided a microarray or membrane for diagnosis of cancer comprising (a) a DNA fragment corresponding to exon 3 of a G-CSF gene, and (b) at least one of DNA fragments corresponding to exons 1, 2, 4 and 5 of said G-CSF gene.

In a still further aspect of the present invention, there is provided a diagnostic agent for cancer comprising an antibody against a mutated G-CSF protein having a deletion of an amino acid sequence corresponding to an exon 3 region of said G-CSF protein.

In a still further aspect of the present invention, there is provided a diagnostic kit for cancer comprising an antibody against a mutated G-CSF protein having a deletion of an amino acid sequence corresponding to an exon 3 region of said G-CSF protein.

In a still further aspect of the present invention, there is provided a microarray or membrane for diagnosis of cancer comprising an antibody against a mutated G-CSF protein having a deletion of an amino acid sequence corresponding to the exon 3 region.

In a still further aspect of the present invention, there is provided a diagnostic method for cancer comprising the steps of: (a) obtaining a G-CSF nucleic acid sample from mammalian tissues or cells; (b) amplifying G-CSF region from the nucleic acid sample obtained, (c) detecting a deletion of exon 3 of said G-CSF gene in the amplified sample.

In a still further aspect of the present invention, there is provided a diagnostic method for cancer comprising the steps of: (a) obtaining a G-CSF protein sample from mammalian tissues or cells; and (b) detecting a deletion of an amino acid sequence corresponding to exon 3 of G-CSF gene in the G-CSF protein sample.

In a still further aspect of the present invention, there are provided primers for use in amplification of G-CSF gene in a G-CSF nucleic acid sample obtained from mammalian tissues or cells.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

The present invention is generally directed to a method for diagnosis and prognosis of cancer by analyzing the presence or absence of exon 3 skipping of G-CSF gene at RNA or protein levels, wherein the G-CSF exon 3 skipping is used as a diagnostic cancer marker.

Colony stimulating factor (CSF), produced in macrophages, T cells and fibroblasts, is widely distributed in a normal body. CSF is largely classified into granulocyte colony-stimulating factor (G-CSF), macrophage colony-stimulating factor (M-CSF) and granulocyte-macrophage colony-stimulating factor (GM-CSF). Of them, G-CSF plays an important role in production of several blood cells during proliferation and differentiation of hemopoietic stem cells. The major role of G-CSF is to increase the number of granulocytes, especially, neutrophils functioning to protect the body against foreign pathogens. The recently widely used chemotherapy for proliferative tumor, which has the effect of inhibiting growth of tumor cells, is disadvantageous in terms of inhibiting division and maturation of neutrophil precursor cells, and thus reducing the immunoprotective ability of patients in response to infection. When administered to patients receiving such chemotherapy, G-CSF is known to be effective in stimulating neutrophil proliferation and thus protecting and treating infectious diseases. In 1986, Nagata et al. reported the nucleotide sequence of human G-CSF gene and its expression in COS cells (Nagata et al., Nature 319:415-418, 1986).

Figure 1:
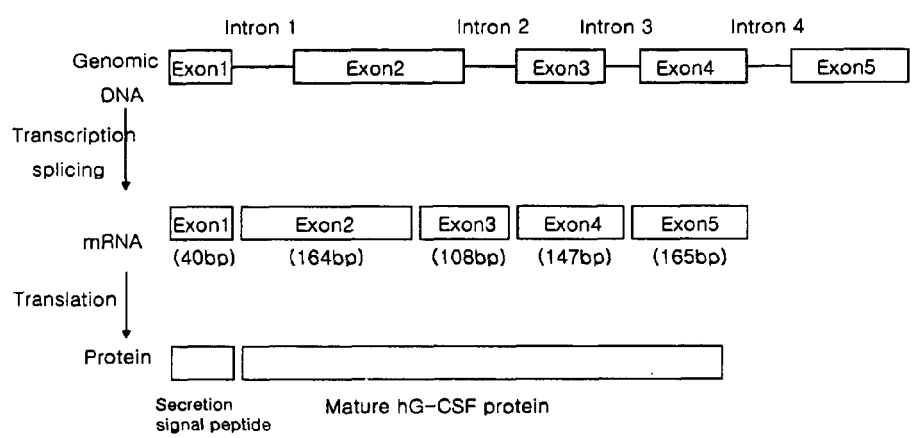
FIG. 1 is a process for normal transcription, splicing and translation of the human G-CSF gene.

Human G-CSF (hG-CSF) is a glycoprotein comprising a secretory signal peptide consisting of 30 amino acids and 174 amino acids, and contains five cystein residues. Four of the five cysteins, forming two disulfide bonds (Cys36-Cys42, Cys64-Cys74), play an important role in folding and biological activity of hG-CSF protein (Hill et al., Proc. Natl. Acad. Sci. USA 90:5167-5171, 1993). With reference to FIG. 1, hG-CSF gene consists of five exons and four introns. A mature hG-CSF mRNA is produced by removing four introns from an hG-CSF mRNA script transcribed from genomic DNA through splicing. The mature hG-CSF mRNA is translated into an hG-CSF precursor protein consisting of 204 amino acids, and a secretory signal peptide of 30 amino acids at the N-terminus is removed from the precursor protein, thereby generating a biologically active hG-CSF protein consisting of 174 amino acids (Nagata et al., EMBO J. 5:575-581, 1986; Hill et al., Proc. Natl. Acad. Sci. USA 90:5167-5171, 1993).

The present inventors discovered, during their research into cloning of hG-CSF gene and production of its translation product, that G-CSF cDNA derived from tumor cells has a deletion of the entire exon 3 region (108 bp). Although deletion of specific exons has been reported in a variety of genes not including G-CSF gene, such deletion in hG-CSF gene has been unknown until now. The hG-CSF protein is known to be present in a form having or not having three amino acids corresponding to the 3' end of exon 2, while being biologically active in both of the two forms (Nagata et al., EMBO J. 5:575-581, 1986). Therefore, a method of diagnosing cancer based deletion of exon 3 of G-CSF gene may be applied to all subtypes of G-CSF according to an identical principle. In addition, since other mammalian-derived G-CSF proteins are known to have almost identical biological activity to the hG-CSF protein, it will be understood by those skilled in the art that a method of diagnosing cancer based on detection of deletion of exon 3 of G-CSF gene according to the present invention can be applied to other mammalian-derived G-CSF proteins according to an identical principle.

Both genes specifically expressed or suppressed in tumor cells, and genetic mutation, can be detected by the conventional molecular biological methods, which are exemplified by (a) polymerase chain reaction (PCR) (Bottema, C. D., Mutat Res. 233:93-102, 1993; Nelson, D. L., Curr. Opin. Genet Dev. 1: 62-68, 1991; Pourzand, C. and Cerutfi, P., Mutat Res. 288:113-121, 1993; and Holland P M et al., Proc. Natl. Acad, Sci. USA 8: 7276-7280, 1991), (b) single-stranded conformation polymorphism (SSCP) (Glavac D., Hum. Mutat. 19:384-394, 2002; Strippoli, P. et al., Int. J. Mol. Med 8:567-572, 2001; and Methods Mol Biol 187:151-63, 2002), (c) DNA sequencing analysis (Sanger, F. et al., Proc. Natl. Acad. Sci USA 74:5463-5467, 1997), (d) protein truncation test (PTI) (Hardy, C. A., Methods Mol. Biol. 187:87-

108, 2002), (e) automatic nucleotide sequence analysis (Boutin P. et al., Hum. Mutat. 15(2):201-203, 2000), (f) study of loss of heterozygosity (LOH) (Yang Q. et al., Clin. Cancer Res. 8:2890-2893, 2002), (g) study of microsatellite instability (MSI) (Furlan, D. et al., J Pathol 197:603-609, 2002), (h) gene analysis using MALDI-TOF (Leushner J., Expert Rev. Mol. Diagn. 1:11-18, 2001), (i) gene analysis by hybridization (Wetmur, J. G., Critical Reviews in Biochem. Mol. Biol. 26:227-259, 1991), (j) gene analysis using DNA chips (Goessl et al., Urology 58:335-338, 2001; Zhou et al., Breast Cancer Res. Treat. 66:217-224, 2001; and C K Kim et al., Korean Pat. Publication No. 2001-0061173), and (k) analysis using protein chips (Pharmacogenomics 1:385-393, 2000). It will be understood by those skilled in the art that deletion of the exon 3 region of G-CSF gene or protein can be easily detected by using the conventional molecular biological methods including the examples as described above. The preferred molecular biological methods used in detecting deletion of the exon 3 region of G-CSF gene or protein include PCR, hybridization, DNA chips, protein chips and enzyme-linked immunosorbent assay (ELISA).

To perform cancer diagnosis according to the present invention, a G-CSF gene or protein sample should first be obtained from tissue specimens or cells. Since a DNA sample for a specific gene is typically obtained from normal tissues or cells at a very small amount, the specific gene should be amplified by PCR, and, for such amplification, suitable primers should be designed. In the present invention, to amplify a part or an entire region of exon 3 of G-CSF gene, nucleic acid fragments to be used as primers in PCR for detection of deletion of exon 3 are necessary. That is, the primers, as used herein, refer to oligonucleotides capable of amplifying a nucleotide sequence of G-CSF gene, comprising a part or an entire region of exon 3. Those skilled in the art will be able to easily design such primers. Therefore, all primers capable of amplifying G-CSF gene comprising a part or an entire region of exon 3, which can be designed by those skilled in the art, are intended to fall within the scope of the present invention. Examples of the primers include oligonucleotides designated as SEQ ID NOs. 1 and 2, which are capable of amplifying a region (Thr1-Pro174) ranging from apart of exon 2 to exon 5 of hG-CSF gene, oligonucleotides designated as SEQ ID NOs. 3 and 5, which are capable of amplifying a region (Ile24-Leu71) ranging from a part of exon 2 to exon 3 of hGCSF gene, and oligonucleotides designated as SEQ ID NOs. 4 and 6, which are capable of amplifying a region (Cys36Ser80) ranging from exon 3 to a part of exon 4 of hG-CSF gene. The present inventors investigated the presence or absence of G-CSF gene and exon 3 in the GCSF gene in mRNA and cDNA samples obtained from 8 normal tissues and 17 tumor cell lines.

In accordance with the present invention, there are provided nucleic acid fragments for use as primer sets in detecting deletion of exon 3 through amplification of the exon 3 region of G-CSF gene, which include, but are not limited to, the following sets, each of which consists of a sense primer and an antisense primer:

```
sense:
5'-ACCCCCCTGGGCCCTGCC-3'          (SEQ ID NO.1)
and antisense:
5'-TCAGGGCTGGGCAAGGTG-3';         (SEQ ID NO.2)
```

```
sense:
5'-ACCCCCCTGGGCCCTGCC-3'          (SEQ ID NO.1)
and antisense:
5'-CAGCTGCAGGGCCTGGCT-3';         (SEQ ID NO.5)

sense:
5'-ACCCCCCTGGGCCCTGCC-3'          (SEQ ID NO.1)
and antisense:
5'-CGCTATGGAGTTGGCTCAAGC-3';      (SEQ ID NO.6)

sense:
5'-ACCCCCCTGGGCCCTGCC-3'          (SEQ ID NO.1)
and antisense:
5'-CAGCTTCTCCTGGAGCGC-3';         (SEQ ID NO.9)

sense:
5'-ATCCAGGGCGATGGCGCAGCG-3'       (SEQ ID NO.3)
and antisense:
5'-TCAGGGCTGGGCAAGGTG-3';         (SEQ ID NO.2)

sense:
5'-ATCCAGGGCGATGGCGCAGCG-3'       (SEQ ID NO.3)
and antisense:
5'-CAGCTGCAGGGCCTGGCT-3';         (SEQ ID NO.5)

sense:
5'-ATCCAGGGCGATGGCGCAGCG-3'       (SEQ ID NO.3)
and antisense:
5'-CGCTATGGAGTTGGCTCAAGC-3';      (SEQ ID NO.6)

sense:
5'-TGTGCCACCTACAAGCTGTGC-3'       (SEQ ID NO.4)
and antisense:
5'-TCAGGGCTGGGCAAGGTG-3';         (SEQ ID NO.2)

sense:
5'-TGTGCCACCTACAAGCTGTGC-3'       (SEQ ID NO.4)
and antisense:
5'-CAGCTGCAGGGCCTGGCT-3';         (SEQ ID NO.5)

sense:
5'-TGTGCCACCTACAAGCTGTGC-3'       (SEQ ID NO.4)
and antisense:
5'-CGCTATGGAGTTGGCTCAAGC-3'.      (SEQ ID NO.6)
```

The nucleic acid fragments include oligonucleotides capable of detecting deletion of exon 3 of G-CSF gene in spite of not containing a nucleotide sequence corresponding to the exon 3 region, wherein the oligonucleotides may contain a nucleotide sequence corresponding to exon 2 or exon 4 of G-CSF gene.

In accordance with an aspect of the present invention, there is provided a gene microarray or membrane to which a DNA fragment comprising a part or an entire region of exon 3 of the G-CSF gene is immobilized, which is useful for diagnosis of cancer. The gene microarray includes DNA chips effective for detection of a gene corresponding to a probe by hybridization including applying an oligonucleotide probe on the surface of a slide glass treated with a specific chemical reagent. Non-limiting examples of the membrane, which can be used instead of the slide glass in hybridization, include all membranes capable of immobilizing DNA fragments, and preferably, nylon and nitrocellulose membranes.

A nucleic acid fragment corresponding to exon 3 of the G-CSF gene is attached on the surface of the microarray according to the present invention, along with one or more nucleic acid fragments selected from the group consisting of nucleic acid fragments corresponding to exons 1, 2, 4 and 5 of the G-CSF gene, wherein each of the nucleic acid fragments used as probes may contain a part or an entire region of its corresponding exon. Non-limiting examples of the nucleic acid fragment corresponding to the exon 3 region, used as a probe in the present invention, include oligonucleotides having a nucleotide sequence designated as SEQ ID NO. 14: TGTGCCACCTACAAGCTGTG, a nucleotide sequence designated as SEQ ID NO. 15: GAGCTGGTGCTGCTCGGACA, a nucleotide sequence designated as SEQ ID NO. 16: GGACACTCTCTGGGCATCCC, and a nucleotide sequence designated as SEQ ID NO. 17: CTGAGCAGCTGCCCCAGCCA. Non-limiting examples of the nucleic acid fragments corresponding to exons 1, 2, 4 and/or 5, which are used as control probes, include oligonucleotides having a nucleotide sequence designated as SEQ ID NO. 10: CTGCAGCTGCTGCTGTGGCAC, a nucleotide sequence designated as SEQ ID NO. 12: AGAAGCTGTGGTGCCAC, a nucleotide sequence designated as SEQ ID NO. 13: TGAGTGAGTGTGCCAC, a nucleotide sequence designated as SEQ ID NO. 18: GCAGGC TGCTTGAGCCAA, a nucleotide sequence designated as SEQ ID NO. 19: AGAAGCTGGCAGGCTG, and a nucleotide sequence designated as SEQ ID NO. 20: TGAGTGAGGCAGGCTG.

Spotting the probes on the surface of a slide glass and a membrane can be easily achieved by the conventional technique known in the art. In addition, preparation of probes, hybridization and stripping will be performed according to the conventional techniques common in the art.

In another aspect of the present invention, there is included a composition for diagnosis of cancer, comprising a DNA fragment containing a part or an entire region of the exon 3 region of G-CSF gene and a diagnostically acceptable carrier. In a further aspect of the present invention, there is included a method of diagnosing cancer employing a mutated G-CSF protein having a deletion of an amino acid sequence corresponding to the exon 3 region of the G-CSF gene, and a polyclonal or monoclonal antibody to the mutated G-CSF protein. The term "a mutated G-CSF protein having a deletion of an amino acid sequence corresponding to the exon 3 region of G-CSF gene", as used herein, refers to a mutated G-CSF protein produced by a deletion in a region ranging from exons 1 to 5 during expression of G-CSF gene, essentially containing a deletion in exon 3. In a still further aspect of the present invention, there is included a diagnostic kit comprising a DNA fragment containing a part or an entire region of exon 3 of the G-CSF gene and a DNA microarray using the DNA fragment. In a still further aspect of the present invention, there is included a diagnostic kit comprising a mutated G-CSF protein having a deletion of an amino acid sequence corresponding to the exon 3 region of the G-CSF gene, and a protein microarray using a polyclonal or monoclonal antibody to the mutated G-CSF protein.

The mutated G-CSF protein having a deletion of an amino acid sequence corresponding to the exon 3 region of the G-CSF gene, and the polyclonal or monoclonal antibody to the mutated G-CSF protein, according to the present invention, may be produced by the conventional method common in the art (Harlow, E. and Lane, D., Antibodies. A Laboratory Manual. Cold Spring Harbor, N.Y.: Cold Spring Harbor Laboratory, 1988; and Wilson, L. and Matsudair, P. eds. Antibodies in Cell Biology (Methods in Cell Biology, Vol. 37). New York: Academic Press, 1933).

Figure 2:
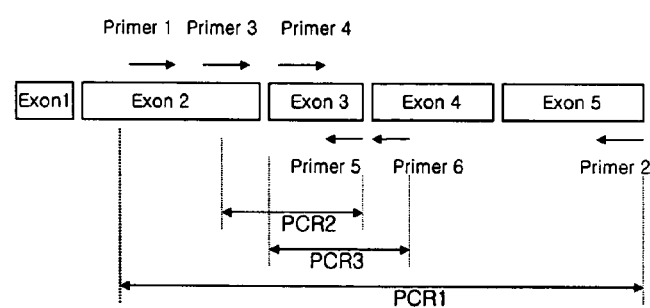
FIG. 2 shows positions of primers used in PCR on a structural map of human G-CSF gene comprising five exons.
Figure 3A:
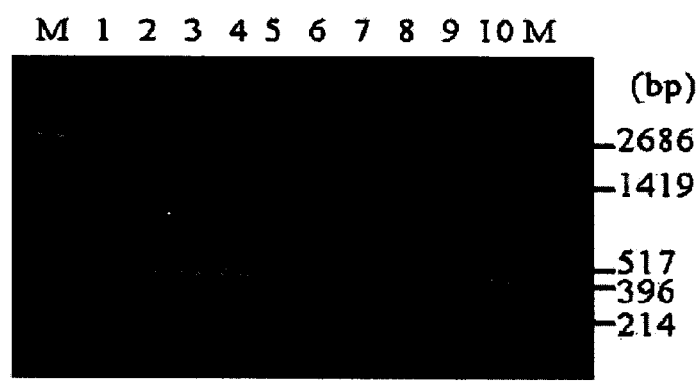
FIG. 3A is a photograph showing PCR1 products separated on an agarose gel (M: size marker, lane 1: normal cell line, lane 2: YCC-7, lane 3: AGS, lane 4: SNU-1, lane 5: MDA-MB-231, lane 6: MCF-7, lane 7: SK-BR-3, lane 8: HT-1080, lane 9: HCT-116, and lane 10: COLO205)
Figure 3B:
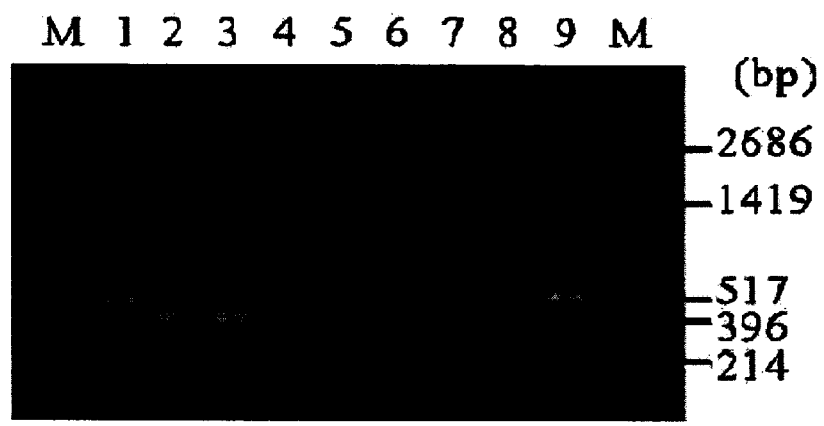
FIG. 3B is a photograph showing PCR1 products separated on an agarose gel (M: size marker, lane 1: normal cell line, lane 2: DLD-1, lane 3: HT-29, lane 4: A549, lane 5: NCI-H460, lane 6: HeLa, lane 7: C-33A, lane 8: B16, lane 9: U-87MG)

In an embodiment of the present invention, when amplifying the exon 3 region of G-CSF gene in mRNA and cDNA samples obtained from 17 tumor cell lines and analyzing the nucleotide sequence of the products, the exon 3 region (108 bp) was found to be deleted in hG-CSF cDNA derived from various tumor cell lines, including stomach cancer cells, breast cancer cells, sarcoma cells, intestinal cancer cells, lung cancer cells, cervical cancer cells and malignant melanoma cells (see, FIGS. 2 and 3). When performing PCR using the hG-CSF cDNA derived from the 17 tumor cell lines as a template with a primer set according to the present invention, it was found that PCR products derived from 16 tumor cell lines are smaller in size than those from a normal cell line, and, as identified by nucleotide sequence analysis of the PCR products, have a deletion of the exon 3 region, among five exons of the normal G-CSF gene.

The deletion of the exon 3 region in G-CSF cDNA can be detected by hybridization. For example, after obtaining a DNA fragment corresponding to exon 3 and a DNA fragment corresponding to exon 2 by performing PCR using normal hG-CSF gene as a template, and immobilizing the two DNA fragments on a nylon membrane, the nylon membrane is hybridized with a cDNA target, derived from a tumor cell line, and deletion of the exon 3 region is determined by detecting binding of the probe with the exon 3 DNA fragment immobilized on the membrane.

The deletion of the exon 3 region in G-CSF cDNA can be detected using a DNA chip, by immobilizing oligonucleotides corresponding to each exon of the G-CSF gene on a slide glass, preparing probes by PCR using exons of the hG-CSF gene as templates, and then reacting the probes with the oligonucleoties.

In addition, deletion of the exon 3 region of G-CSF may be easily detected by preparing a recombinant G-CSF protein using a mutated G-CSF nucleotide sequence having a deletion of the exon 3 region, preparing a polyclonal or monoclonal antibody to the recombinant mutated G-CSF protein, and comparing the mutated G-CSF protein levels in normal individuals and cancer patients by ELISA using the antibody.

In another aspect, the present invention includes an immunochromatographic assay. The representative example of the assay is the lateral flow immunoassay. A diagnostic kit for lateral flow immunoassay comprises a sample pad to which a specimen is loaded, a releasing pad coated with an antibody as a probe, a membrane (mainly, nitrocellulose) or strip for development of the sample, in which the specimen migrates and is separated and antibody-antigen reaction occurs, and an absorption pad for driving continuous migration of the specimen. The antibody used as a probe is labeled by being immobilized on, for example, colloidal gold particles. Instead of the colloidal gold particles, latex beads or carbon particles are available. The diagnostic kit for lateral flow immunoassay is typically designed to detect an analyte in a sandwich form. The analyte contained in the specimen is applied to the sample pad, migrates and reacts with the antibody coated on the releasing pad, forming antigen-antibody complexes. The formed complexes further migrate and are captured by an additional antibody immobilized on the membrane for development, generating triplexes of sandwich form. That is, since the additional antibody is immobilized on the membrane for development, the triplexes are accumulated on the surface of the membrane, on which the additional antibody is immobilized. Since proteins are not visible to the naked eye, formation of triplexes and their amount are determined by amount of gold particles conjugated to the antibody contained in the triplexes.

In accordance with another aspect of the present invention, there is provided a method of diagnosing cancer based on detection of deletion of the exon 3 region of G-CSF gene. In detail, in accordance with the present invention, diagnosis of cancer may be achieved by obtaining a nucleic acid sample from animal tissues or cells, and detecting deletion of the exon 3 region of G-CSF gene in the nucleic acid sample using a molecular method. Human tissues or cells as a source of the nucleic acid sample include biological fluid samples, biopsy specimens, solid phase tissue samples such as tissue culture or the tissue-derived cells, and offsprings of the cells. In addition, the sample sources include chemical reagent-treated, solubilized samples, cultured cells, cell culture supernants, and cell lysates. In more detail, in terms of objects of the present invention, the human tissues or cells include tumor tissues or tissues considered to be neoplastic, and may be obtained by conventional methods common in the art, such as surgical resection, biopsies or suction. From the human tissues or cells, a nucleic acid sample may be obtained by the conventional method known in the art.

The method of diagnosing cancer based on detection of deletion of exon 3 of G-CSF gene according to the present invention may be, as described above, achieved by nucleotide sequence analysis of the G-CSF gene, as well as by using a specific probe to a region corresponding to the exon 3 region of the G-CSF gene, for example, by employing an antibody specific to a mutated G-CSF protein having a deletion of an amino acid sequence corresponding to the exon 3 region.

The method of diagnosing cancer of the present invention may be used in diagnosis of various cancers, including stomach cancer, breast cancer, sarcoma, intestinal cancer, lung cancer, cervical cancer, liver cancer, prostate cancer, tongue cancer, laryngeal cancer, pharyngeal cancer, oral cancer, thyroid cancer, colorectal cancer, esophageal cancer, and testicular cancer.

The present invention will be explained in more detail with reference to the following examples in conjunction with the accompanying drawings. However, the following examples are provided only to illustrate the present invention, and the present invention is not limited to them.

Example 1

Preparation of mRNA and cDNA from Tumor Cell Lines mRNA and cDNA samples were prepared from 8 normal cell lines and tissues, and 17 tumor cell lines. The normal cell lines and tumor cell lines used in Examples of the present invention are given in Table 1, below.

TABLE 1

Normal and tumor cell lines used in the present invention

| | | Cell types | Cell collection centers |
|---|---|---|---|
| Tumor cell line | YCC-7 | Stomach cancer cell line | Cancer metastasis research center, College of Medicine, Yonsei University |
| | AGS | Stomach cancer cell line | ATCC CRL-1739 |
| | SNU-1 | Stomach cancer cell line | Korean Cell Line Research Foundation (KCLRF), Seoul National University |
| | MDA-MB-231 | Breast cancer cell line | ATCC HTB-26 |
| | MCF-7 | Breast cancer cell line | ATCC HTB-22 |
| | SK-BR-3 | Breast cancer cell line | ATCC HTB-30 |
| | HT-1080 | Sarcoma cell line | ATCC CCL-121 |
| | HCT-116 | Colon cancer cell line | ATCC CCL-247 |
| | COLO205 | Colon cancer cell line | ATCC CCL-222 |
| | DLD-1 | Colon cancer cell line | ATCC CCL-221 |
| | HT-29 | Colon cancer cell line | ATCC HTB-38 |
| | A549 | Lung cancer cell line | ATCC CCL-185 |
| | NCI-H460 | Lung cancer cell line | ATCC HTB-177 |
| | HeLa | Cervical cancer cell line | ATCC CCL-2 |
| | C-33A | Cervical cancer cell line | ATCC HTB-31 |
| | B16 | Malignant melanoma cell line | ATCC CRL-6322 |
| | U-87MG | Brain cancer cell line | ATCC HTB-14 |
| Normal cell line | 293 | Human kidney embryonic cell line | Cancer metastasis research center, College of Medicine, Yonsei University |
| | Sample 1 | Human lymphocytes | Cancer metastasis research center, College of Medicine, Yonsei University |
| | Sample 2 | Human monocytes | Cancer metastasis research center, College of Medicine, Yonsei University |
| | Sample 3 | Human epidermis tissues | Cancer metastasis research center, College of Medicine, Yonsei University |
| | Sample 4 | Human dermis tissues | Cancer metastasis research center, College of Medicine, Yonsei University |
| | Sample 5 | Human hair pollicle cells | Cancer metastasis research center, College of Medicine, Yonsei University |
| | Sample 6 | Human fat cells | Cancer metastasis research center, College of Medicine, Yonsei University |
| | Sample 7 | Human muscle cells | Cancer metastasis research center, College of Medicine, Yonsei University |

The tumor cell lines listed in Table 1 can be obtained from the cell collection centers listed in Table 1. In addition, human normal cell lines, lymphocytes, monocytes, epidermis, dermis, hair follicles, fat cells and muscle cells can be easily obtained from the cancer metastasis research center at College of Medicine, Yonsei University. The tumor cell line YCC-7, obtained from the cancer metastasis research center, was prepared as follows. Ascitic fluid was aseptically obtained from advanced cancer patients, and supplemented with heparin in an amount of 10 units per ml to prevent clumping of cells. After centrifugation at 400×g for 10 min, the precipitated cells were cultured in a culture flask of 25 $cm^3$. In case of containing a large number of erythrocytes, Ficoll-hypaque density gradient centrifugation at 800×g was performed to separate mononuclear cells from erythrocytes, and the obtained mononuclear cell phase was incubated at 37° C. under 5% $CO_2$. After incubation for 16-18 hrs, the culture medium was centrifuged at 400×g for 10 min, and the precipitated cells were cultured in a new culture flask of 25 $cm^3$. During culturing, cells were observed under a phase contrast microscope, and the culture medium was replaced twice or three times per week. When tumor cell colonies were formed, the tumor cell clusters were obtained by treatment with trypsin-EDTA or by using scrapers, and the fluid containing tumor cells was centrifuged to remove normal cells. The resulting pure tumor cells were stored at frozen states according to their passages.

Total RNA was isolated from each tumor cell line, normal cell line and normal tissue using Tri-Reagent (Gibco-BRL, USA). 1 ml of Trizol Reagent was added to a tissue sample ground after quickly freezing using liquid nitrogen, followed by incubation at room temperature for 5 min. The resulting tissue sample was supplemented with 0.2 ml of chloroform, vigorously mixed for 15 sec, and incubated at room temperature for 5 min. After centrifugation at 12,000×g at 4° C. for 15 min, the resultant aqueous phase was transferred to a new tube. An equal volume of isopropanol was added to the tube, and the tube was placed at 4° C. for 10 min. After centrifugation at 12,000×g at 4° C. for 10 min, the supernatant was carefully discarded, and the pellet was washed with 70% ethanol, followed by centrifugation at 7,500×g at 4° C. for 5 min. After being dried, the RNA pellet was dissolved in RNase-free water.

To synthesize cDNA from mRNA isolated from each cell line, and human-derived tumor and normal cell line, RT-PCR was performed as follows. 2 μg of total RNA was mixed with 1 μl of an oligo(dT)$_{16}$-primer, and RNase-free water was added up to a final volume of 11 μL. This mixture was heated at 90° C. for 5 min, and placed on ice, immediately after completion of the heating. After putting 4 μl of a reaction buffer, 2 μl of 10 mM dNTPs, 1 μl of RNase inhibitor and 2 μl of reverse transcriptase into another tube, 8.5 μl of the RNA mixture was added to the pre-mixture tube, followed by incubation at room temperature for 10 min. The reaction mixture was incubated at 42° C. for 90 min and then at 95° C. for 15 min. Immediately after the incubation at 95° C., the mixture was placed on ice to terminate reaction, thus yielding a cDNA sample.

Example 2

Detection of hG-CSF Gene by PCR

In order to detect expression of normal hG-CSF gene in each tumor cell line, PCR was carried out using cDNA prepared in Example 1 as a template. As shown in FIG. 2, PCR reactions were divided into three types according to their amplified products, as follows: PCR 1 for amplification of a region (Thr1-Pro174) ranging from a part of exon 2 to exon 5 of hG-CSF gene; PCR 2 for amplification of a region (Ile24-Leu71) ranging from a part of exon 2 to exon 3 of hG-CSF gene; and PCR 3 for amplification of a region (Cys36-Ser80) ranging from exon 3 to a part of exon 4 of hG-CSF gene.

PCR 1 was carried out using a cDNA sample from each tumor cell line as a template, and a primer set of a sense primer designated SEQ ID NO.: 1 (5'-ACCCCCCTGGGC-CCTGCC-3) and an antisense primer designated SEQ ID NO.: 2 (5'-TCAGGGCTGGGCAAGGTG-3). PCR 2 was carried out using a cDNA sample from each tumor cell line as a template, and a primer set of a sense primer designated SEQ ID NO.: 3 (5'-ATCCAGGGCGATGGCGCAGCG-3) and an antisense primer designated SEQ ID NO.: 5 (5'-CAGCTG-CAGGGCCTGGCT-3'). PCR 3 was carried out using a cDNA sample from each tumor cell line as a template, and a primer set of a sense primer designated SEQ ID NO.: 4 (5'-TGTGCCACCTACAAGCTGTGC-3) and an antisense primer designated SEQ ID NO.: 6 (5'-CGCTATGGAGTTG-GCTCAAGC-3'). PCR was performed using a high fidelity PCR system (Boehringer Mannheim Co., Germany) under the following condition. PCR conditions included denaturation at 94° C. for 7 min, and 30 cycles of denaturation at 94° C. for 40 sec, annealing at 56° C. for 40 sec and extension at 72° C. for 1 min, followed by final extension at 72° C. for 7 min.

Figure 6A:
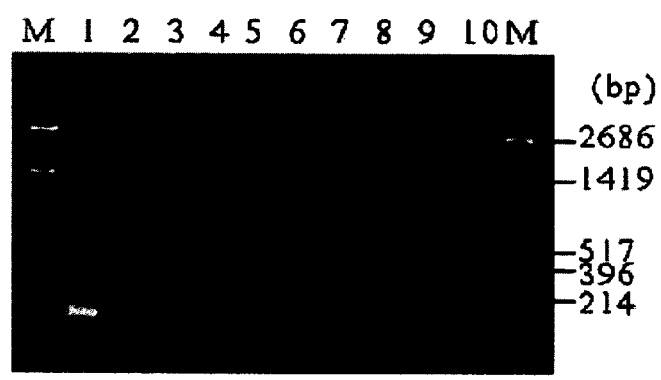
FIG. 6A is a photograph showing PCR2 products separated on an agarose gel (each lane is the same cell line as in FIG. 3A)
Figure 6B:
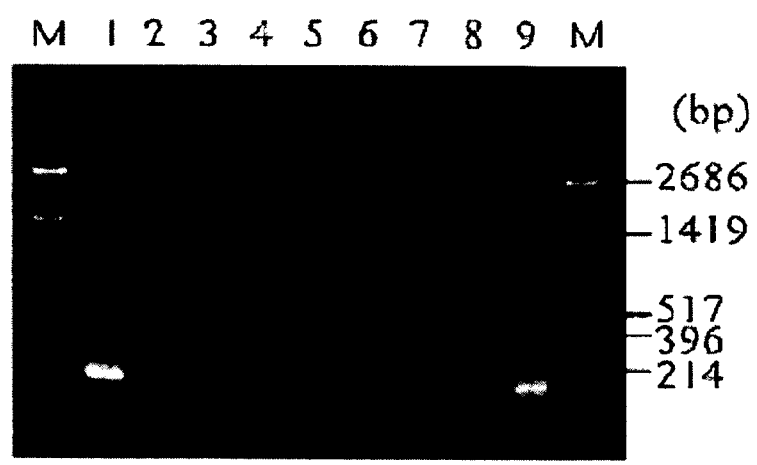
FIG. 6B is a photograph showing PCR2 products separated on an agarose gel (each lane is the same cell line as in FIG. 3B)
Figure 7A:
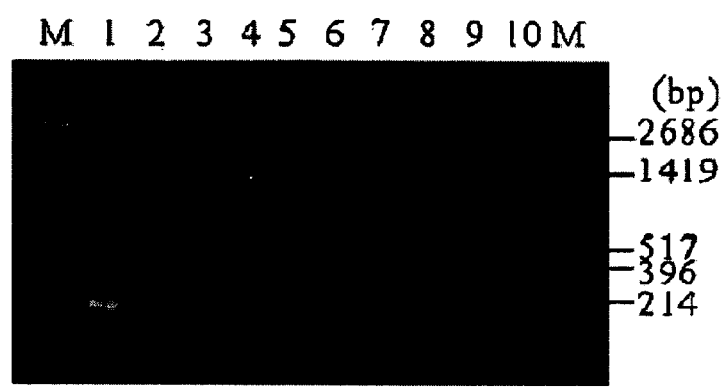
FIG. 7A is a photograph showing PCR3 products separated on an agarose gel (each lane is the same cell line as in FIG. 3A)
Figure 7B:
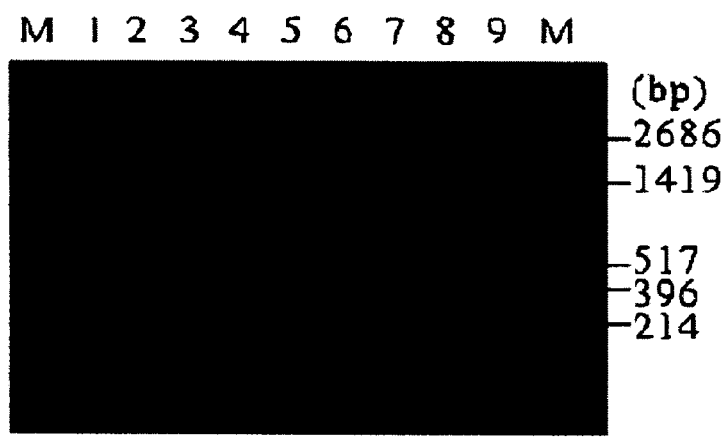
FIG. 7B is a photograph showing PCR3 products separated on an agarose gel (each lane is the same cell line as in FIG. 3B)

PCR products were separated on an agarose gel. As a result of electrophoresis, in the case of PCR1, PCR products from tumor cell lines were found to be smaller in size than a normal G-CSF gene, except that a PCR product from U-87MG has a size equal to that of normal G-CSF gene (see, FIG. 3A in which M: size marker, lane 1: normal cell line, lane 2: YCC-7, lane 3: AGS, lane 4: SNU-1, lane 5: MDA-MB-231, lane 6: MCF-7, lane 7: SK-BR-3, lane 8: HT-1080, lane 9: HCT-116, and lane 10: COLO205; and FIG. 3B in which M: size marker, lane 1: normal cell line, lane 2: DLD-1, lane 3: HT-29, lane 4: A549, lane 5: NCI-H460, lane 6: HeLa, lane 7: C-33A, lane 8: B16, and lane 9: U-87MG). In the cases of PCR2 and PCR3, a PCR product was generated only from U-87MG cells, while PCR products were not obtained in other tumor cell lines (see, FIGS. 6 and 7). In addition, the PCR product of U-87MG cells, produced in PCR2 and PCR3, was found to have a size equal to that of the PCR product of normal cells.

Figure 4:
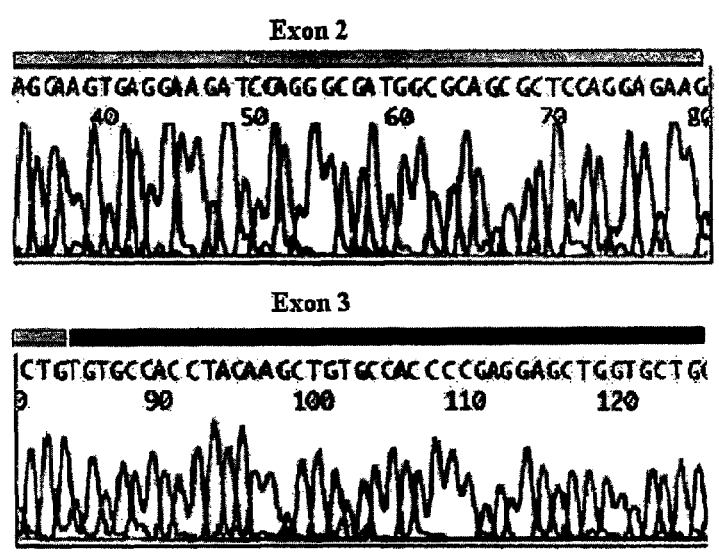
FIG. 4 shows a result of nucleotide sequence analysis of human G-CSF gene derived from normal cells.
Figure 5:
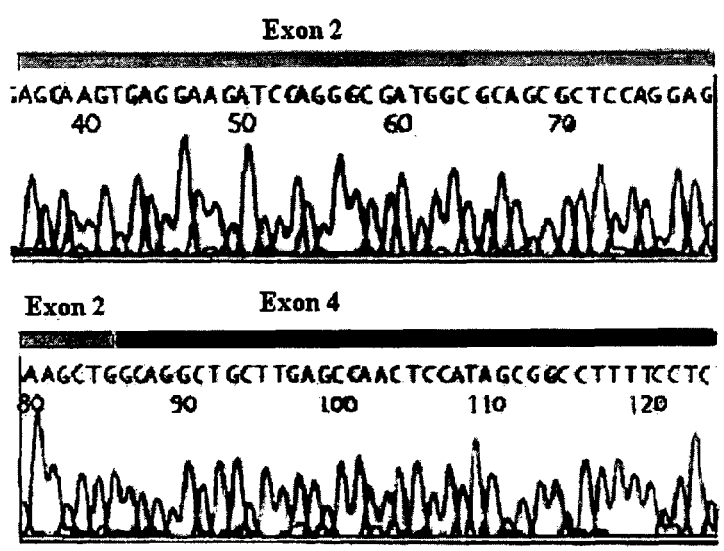
FIG. 5 shows a result of nucleotide sequence analysis of human G-CSF gene derived from tumor cells.

Nucleotide sequences of PCR1 products were analyzed using an automatic DNA sequencer (ABI Prism model 377, Perkin Elmer Co., USA). As a result of nucleotide sequence analysis, the PCR product obtained from U-87MG cells was found to have a nucleotide sequence (SEQ ID NO.: 7) identical to that of G-CSF gene of normal cells. In contrast, PCR products obtained from other tumor cell lines, compared with the nucleotide sequence of G-CSF of normal cells, was found to have a nucleotide sequence (SEQ ID NO.: 8) having a deletion of 108 bp (see, FIGS. 4 and 5). When comparing the deleted 108 bp with the nucleotide sequence of G-CSF, the deleted 108 bp was found to correspond to the exon 3 region among five exons.

In order to investigate whether tissues of normal individuals display the same PCR result as obtained from the normal cell line, when RT-PCR was carried out using RNA isolated from lymphocytes, monocytes, epidermis tissues, dermis tissues, hair follicles, fat cells and muscle cells of normal individuals, and PCR was carried out using cDNA obtained from the RT-PCR, no deletion of exon 3 was found in cells and tissues from normal individuals, indicating that the deletion of exon 3 found in PCR products of tumor cell lines is not induced by PCR error. In addition, a mutated G-CSF protein expressed from G-CSF cDNA having a deletion of exon 3 is highly likely to have lost active site function and to have a different conformation from the normal G-CSF protein. Therefore, it is believed that G-CSF protein expressed in tumor cells does not exhibit normal function.

Example 3

Detection of G-CSF Gene by Hybridization

The deletion of exon 3 in G-CSF cDNA from tumor cell lines was detected by hybridization.

PCR was carried out using G-CSF gene derived from a normal cell line as a template, and a primer set of a sense primer designated SEQ ID NO.: 4 (5'-TGTGCCACCTA-CAAGCTGTGC-3) and an antisense primer designated SEQ ID NO.: 5 (5'-CAGCTGCAGGGCCTGGCT-3). A DNA fragment of 108 bp corresponding to the exon 3 region of G-CSF gene was obtained.

Separately, PCR was carried out using G-CSF gene derived from the normal cell line as a template, and a primer set of a sense primer designated SEQ ID NO.: 1 (5'-AC-CCCCTGGGCCCTGCC-3) and an antisense primer designated SEQ ID NO.: 9 (5'-CAGCTTCTCCTGGAGCGC-3). A DNA fragment of 105 bp corresponding to the exon 2 region of G-CSF gene was obtained.

After being purified, each of the DNA fragments (50 ng/μl) was spotted on a nylon membrane (Boehringer Mannheim, Germany), and incubated at 80° C. for 2 hrs to immobilize it onto the membrane.

Target probes for hybridization of the DNA fragments corresponding to exon 2 and exon 3, immobilized on the membrane, were prepared by RT-PCP RT-PCR was performed as follows. First, a reaction mixture A (2 μg of total RNA, 1 μl of an oligo(dT)$_{16}$-primer, total volume: 15 μl) was incubated at 94° C. for 2 min to denature RNA, and then slowly cooled to 42° C. over about 20 min. Another reaction mixture B (333 μM of each of DATP, dGTP and dCTP, 1× reverse transcriptase buffer, 20 μCi of [α-$^{32}$P] dCTP (2,000-3,000 Ci/mmol), 50 U of AMV reverse transcriptase, total volume: 30 μl) was added to the mixture A, and reverse transcription was carried out at 42° C. for 2 hrs. Thereafter, dNTP, including [α-$^{32}$P] dCTP, not participating in polymerization were removed using a QIAquick Nucleotide Removal Kit (Qiagen, USA).

Using the cDNA probe, hybridization was carried out on the nylon membranes on which the DNA fragments corresponding to exons 2 and 3 of G-CSF are immobilized. First, after being immersed in 2×SSPE buffer (1×SSPE: 0.18M NaCl, 10 mM sodium phosphate, 1 M EDTA, pH 7.7) for 5 min. the nylon membranes were treated with 2 ml of a hybridization solution (5×SSPE, 2% SDS, 1×Denhardt's reagent, sonicated and 100 μg/ml denatured salmon sperm DNA) preheated to 65° C., where the membranes were sealed in a vinyl bag. After incubation at 65° C. for 1 hr, a denatured cDNA probe, prepared by mixing 10 μl of the cDNA probe with 0.5 ml of the hybridization solution and then boiling the mixture for 10 min, was added to the hybridization solution in which the membranes were immersed, followed by incubation at 65° C. for 18 hrs to allow hybridization. Thereafter, the membranes were washed three times with a washing solution (0.5×SSPE, 0.2% SDS) at 65° C. for 30 min. Radioactivity was detected by exposing the membranes or X-ray film and developing the film.

Figure 8:
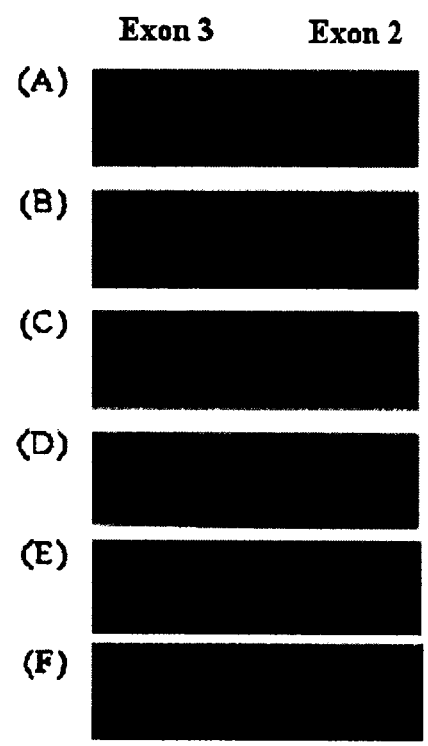
FIG. 8 shows a result of hybridization of exon 2 DNA and exon 3 DNA bound to a nylon membrane with targets derived from tumor cells (A: YCC-7, B: AGC, C: HT-29, D: A549, E: MCF-7, and F: U-87MG)

As shown in FIG. 8, in the case of probes prepared using total RNA firm tumor cell lines, YCC-7, AGS, HT-29, A549 and MCF-7, the probes were found to bind to the DNA fragment of exon 2, but not to bind to the DNA fragment of exon 3 (see, FIGS. 8A, 8B, 8C, 8D and 8E). In contrast, a probe prepared using total RNA from U-87MG cells known to contain normal G-CSF gene was found to bind the two DNA fragments of exons 2 and 3 (see, FIG. 8F). As described above, it was demonstrated that deletion of exon 3 of G-CSF can be easily detected by hybridization. The hybridization method is applicable to detection methods using the recently developed DNA microarray. Therefore, it is believed that a variety of detection methods using the hybridization method can be easily developed, and that cancer can be diagnosed easily and accurately by the detection methods.

Example 4

Detection of G-CSF Gene Using a DNA Chip for Detection of Deletion of Exon 3 of G-CSF In order to investigate whether a DNA chip can be used as a tool for detection of deletion of exon 3 of G-CSF mRNA or cDNA, various DNA fragment probes capable of being immobilized on a glass plate was prepared as follows.

One probe corresponding to a part of exon 2 of G-CSF, four non-overlapping probes corresponding to exon 3, and one probe corresponding to a part of exon 4, were designed to consist of 20 nucleotides each. In addition, one probe corresponding to a region continuously ranging from a part of exon 2 to a part of exon 3, one probe corresponding to a region continuously ranging from a part of exon 3 to a part of exon 4, and one probe corresponding to a region continuously ranging from a part of exon 2 to a part of exon 4, were designed to have 8 nucleotides of each exon. Since two different G-CSF mRNAs (human G-CSFa and human G-CSFb mRNAs) are generated by alternative splicing in the exon 2 region (Tshuchiya M. et al., EMBO J 5:575-581, 1986), two types of probes comprising a region corresponding to exon 2 were prepared, based on the two different G-CSF mRNAs.

To confer ability to be immobilized on a glass plate, when synthesizing all DNA fragment probes, a base having an amino group was inserted to the 3' end of each of the probes using an aminolinker column (Cruachem, Glasgrow, Scotland), and slide glass coated with aldehyde residues (CEL Associates, Inc., Houston, Tex., USA) were used. After being dissolved in 3×SSC (0.45M NaCl, 15 mM $C_6H_5Na_3O_7$, pH 7.0), the DNA probes were immobilize on the slide glass by accumulating the DNA probes using a microarrayer manufactured by the present inventors (Yoon et al, J. Microbiol. Biotechnol. 10:21-26, 2000), and reacting for over 1 hr under about 55% humidity, and then leaving the glass at room temperature for 6 hrs. Herein, the probes were arranged at intervals of 275 μm on the glass at an amount of 100 μM, thus producing a microarray.

Immobilization of probes through reaction between amine groups of probes and aldehyde groups on the glasses was estimated by staining with SYBRO green II (Molecular Probe, Inc., Leiden, Netherlands).

A gene fragment as a probe, to be immobilized on a glass, was prepared by asymmetric PCR using G-CSF gene extracted from each cell line, and a primer set of a sense primer designated SEQ ID NO.: 10 (5'-CTGCAGCTGCT-GCTGTGGCAC-3') and an antisense primer designated SEQ ID NO.: 11 (5'-FITC-CTGCTGCCAGATGGTGGT-3') in a ratio of 1:5, wherein the gene fragment was obtained by performing PCR once. Information on probes immobilized on the slide glass is given in Table 2, below.

TABLE 2

| Nucleotide sequences | Corresponding regions on hG-CSF gene | SEQ ID NOs. |
|---|---|---|
| CTGCAGCTGCTGCTGTGGCAC | Exon 2 | 10 |
| AGAAGCTGTGGTGCCAC | Exons 2 to 3 (hG-CSFa) | 12 |
| TGAGTGAGTGTGCCAC | Exons 2 to 3 (hG-CSFb) | 13 |
| TGTGCCACCTACAAGCTGTG | Exon 3 | 14 |
| GAGCTGGTGCTGCTCGGACA | Exon 3 | 15 |
| GGACACTCTCTGGGCATCCC | Exon 3 | 16 |
| CTGAGCAGCTGCCCCAGCCA | Exon 3 | 17 |
| GCAGGCTGCTTGAGCCAA | Exon 4 | 18 |
| AGAAGCTGGCAGGCTG | Exons 2 to 4 (hG-CSFa) | 19 |
| TGAGTGAGGCAGGCTG | Exons 2 to 4 (hG-CSFb) | 20 |

Asymmetric PCR was carried out under the conditions of denaturation at 94° C. for 5 min, 10 cycles of denaturation at 94° C. for 1 min, annealing at 56° C. for 1 min and extension at 72° C. for 30 sec, and 30 cycles of denaturation at 94° C. for 1 min, annealing at 58° C. for 1 min and extension at 72° C. for 30 sec, followed by final extension at 72° C. for 7 min.

PCR products were separated on an agarose gel. From the result of electrophoresis, double stranded DNA and single stranded DNA figments were produced in each PCR sample. After amplifying G-CSF gene by asymmetric PCR using a plasmid carrying exon 3-deleted G-CSF gene and another plasmid carrying G-CSF having no deletion of exon 3, the two amplified products were analyzed using a DNA chip. A hybridization solution (6×SSPE, 20% (v/v) formamide) was added to 15 µl of the amplified product up to a final volume of 200 µl. The mixture was applied on a slide glass having an immobilized probe, and the glass was covered with a probe-clip press-seal incubation chamber (Sigma Co., St. Louis, Mo.), followed by incubation in a shaking incubator at 30° C. for 6 hrs to induce binding of the probe to the amplified product. Thereafter, the glass was washed over 5 min with 3×SSPE (0.45M NaCl, 15 mM $C_6H_5Na_3O_7$, pH 7.0), 2×SSPE (0.3M NaCl, 10 mM $C_6H_5Na_3O_7$, pH 7.0), and then 1×SSPE (0.15M NaCl, 5 mM $C_6H_5Na_3O_7$, pH 7.0), and scanned using scanarray 5000 (GSI Lumonics Inc., Bedford, Mass.).

Figure 9:
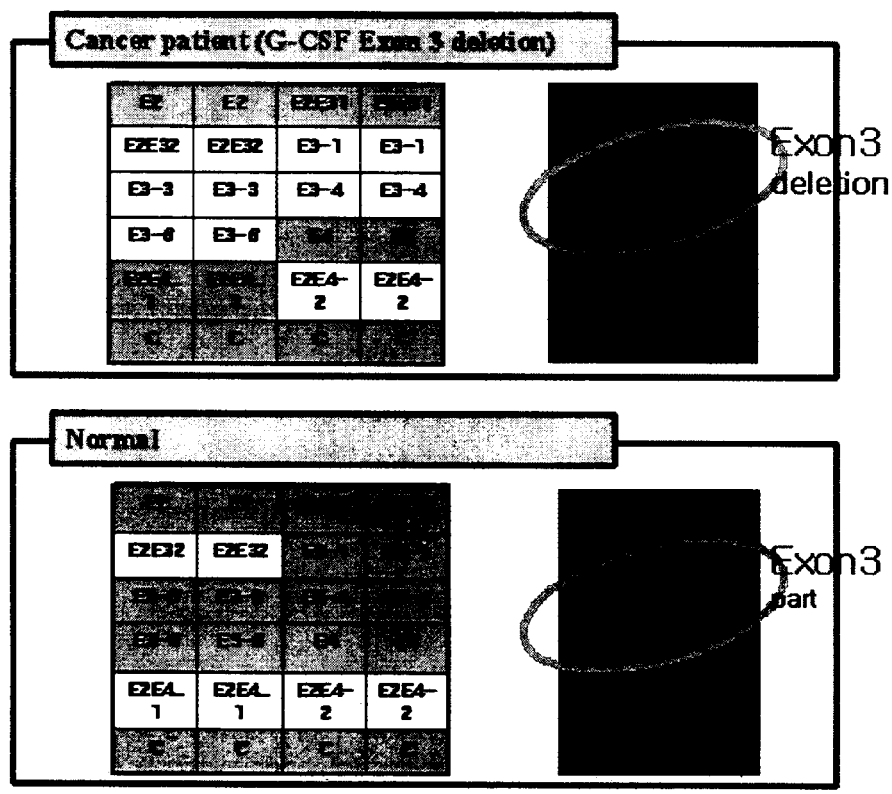
FIG. 9 shows a result of analysis of deletion of exon 3 of G-CSF gene by a DNA chip.

As shown in FIG. 9, in case of the plasmid having no deletion of exon 3 in G-CSF gene, signals was detected for all probes. In contrast, in case of the exon 3-deleted G-CSF-containing plasmid, signals were detected on exon 2 and exon 4 region, wherein the plasmid has a nucleotide sequence corresponding to G-CSFa-type RNA.

These results indicate that DNA chips capable of detecting deletion of the exon 3 region of G-CSF mRNA or cDNA can be developed using the above mentioned primers and probes.

Example 5

Production of a Recombinant Mutated G-CSF Protein

To produce a mutated G-CSF protein in a large scale by recombinant *E. coli*, fed-batch fermentation of *E. coli* BL21 (DE3) (Novagen Inc., USA) carrying a recombinant plasmid pED-CSF4BLIIE was performed. The pED-CSF4BLIIE plasmid was prepared by cloning a nucleotide sequence corresponding to a mutated G-CSF protein having a deletion of the exon 3 region into a plasmid pET21c (Novagen Inc., USA), as follows. First, PCR was carried out using human breast cancer cDNA library as a template, and a primer set of primer 1 (forward primer) containing an EcoRI site: 5'-GC-GAATTCATGGCTGGACCTGCCACCCAG-3' and primer 2 (reverse primer) containing a BamHI site: 5'-GCGGATC-CTTATTAGGGCTGGGCAAGGTGGCG-3'

Figure 12:
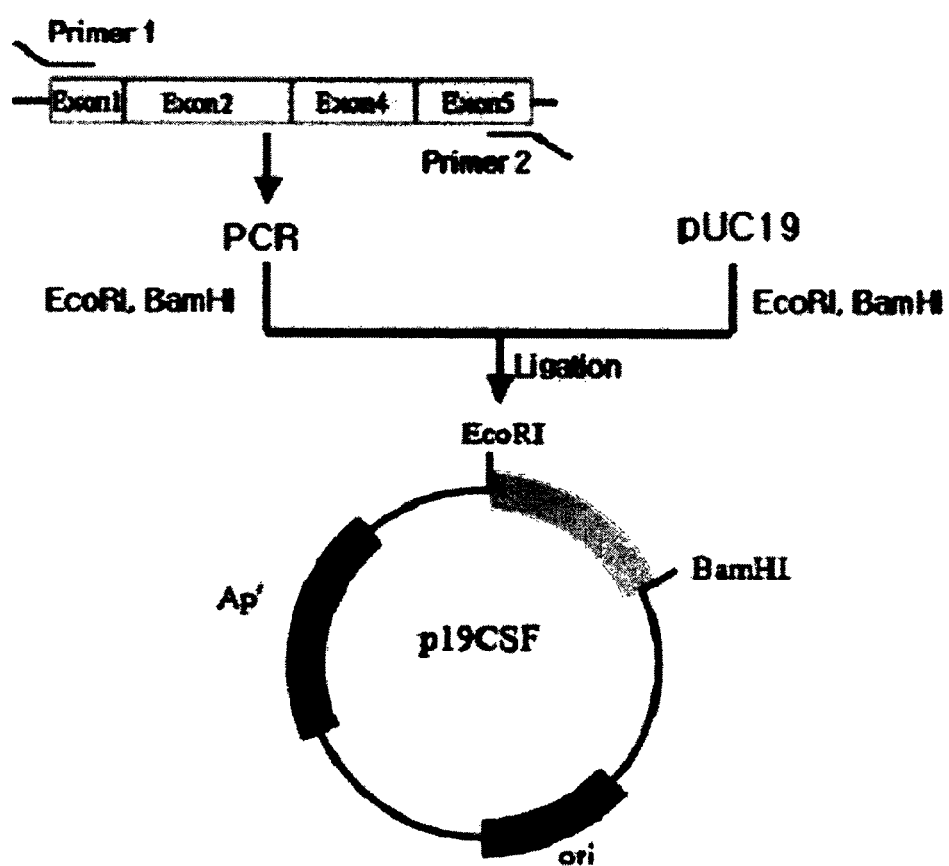
FIG. 12 is a process for construction of plasmid p19CSF.

A PCR product was treated with EcoRI and BamHI, and cloned into pUC19 (Stratagene, USA), thus giving a plasmid p19CSF (see, FIG. 12). The G-CSF gene cloned into pUC19 does not contain the exon 3 region.

Using the plasmid p19CSF as a template, PCR was carried out with a primer set of primer 4 (forward primer): 5'-GC-GAATTCATATGACCCCCCTGGGCCCTGCCA GC-3' and primer 2 (reverse primer): 5'-GCGGATCCTTATT-AGGGCTGGGCAAGGTGGCG-3'.

Figure 13:
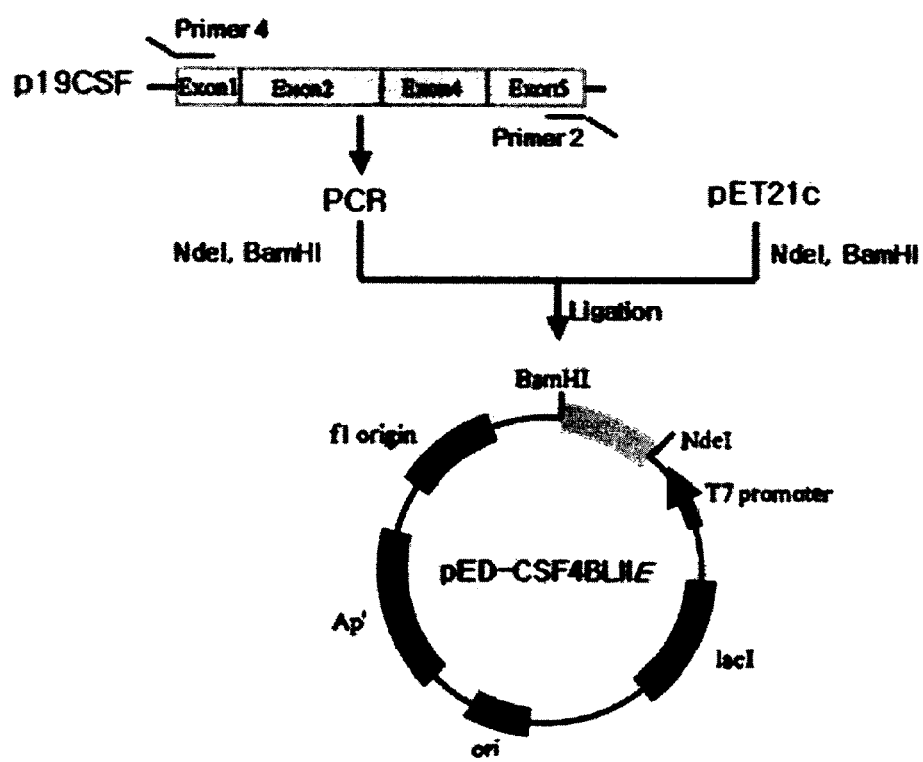
FIG. 13 is a process for construction of recombinant plasmid pED-CSF4BLIIE expressing a mutated G-CSF protein having a deletion of the amino acid sequence corresponding to exon 3.

A PCR product was treated with NdeI and BamHI, and cloned into plasmid pET21c. To change a codon corresponding to the first amino acid to a codon optimal in the bacterial translation system, PCR was carried out again using as the forward primer a primer: 5'-GCGAATTCATATGACTC-CGTTAGGTCCAGCCAGC-3' instead of the primer 4: 5'-GCGAATTCATATGACCCCCCTGGGCCCTGCCAGC-3' the produced DNA fragment was treated with NdeI and BamHI, and cloned into a plasmid pET21c, thus giving a plasmid pED-CSF4BLIIE (see, FIG. 13). Nutrients and additional substances, used for fed-batch fermentation, are given in Table 3, below.

TABLE 3

| Culture medium | | Additionally supplied solution | |
|---|---|---|---|
| Nutrients | Conc. (g/L) | Substances | Conc. (g/L) |
| $(NH_2)_2HPO_4$ | 3.0 | Glucose | 700.0 |
| $KH_2PO_4$ | 7.0 | $MgSO_4.7H_2O$ | 15.0 |
| $MgSO_4.7H_2O$ | 1.0 | Yeast extract | 50.0 |
| Citric acid | 0.8 | | |
| Yeast extract | 2.0 | | |
| Glucose | 20.0 | | |
| Trace metal solution | 3 (ml) | | |

Figure 10:
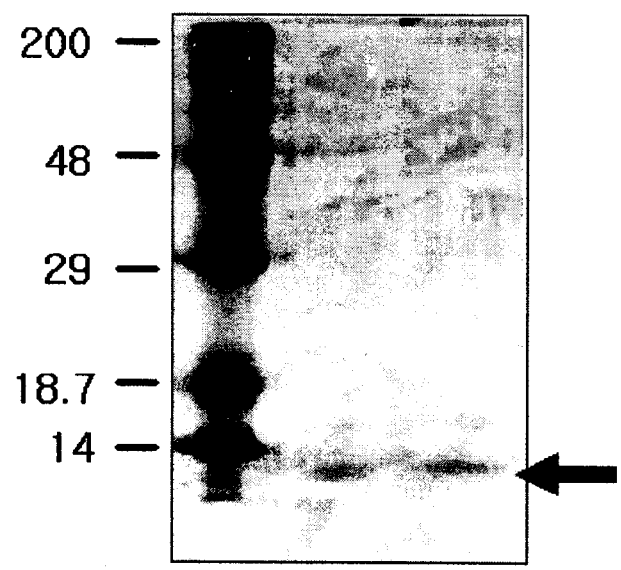
FIG. 10 shows a result of SDS-PAGE of a purified recombinant mutated G-CSF protein having a deletion of an amino acid sequence corresponding to the exon 3 region.

*E. coli* BL21(DE3) cells transformed with the plasmid pED-CSF4BLIIE were incubated in a 250 ml flask with agitation at 37° C. for 8 hrs. 200 ml of the culture was inoculated into 1.8 L of a culture medium contained in a 5 L fermentor (NBS fermentor), and cultured at 37° C., where pH of the medium was constantly maintained at 6.8. pH was maintained using a 28% NOH solution. Pure oxygen was optionally supplied. Supply of additional substances was controlled by a pH-stat. That is, when pH increased to 6.88, 2-3 g of glucose, 0.3 g of yeast extract and 0.1 g of $MgSO_4.7H_2O$ were automatically added. During culturing, glucose concentration was maintained below 5 g per liter. When $OD_{600}$ reached 30, 1 mM IPTG (isopropyl-β-D-thiogalactopyranoside) was added to the medium to induce high growth of bacteria, thus producing a high concentration bacteria culture having an $OD_{600}$ value of 90. Amount of produced mutated G-CSF protein was evaluated by measuring intensity of a protein band using a densitometer (see, FIG. 10). Normal mature G-CSF protein has a molecular weight of about 18.7 kDa, and the mutated G-CSF protein translated from the exon 3-deleted G-CSF cDNA has a molecular weight of about 13 kDa.

Example 6

Preparation of a Polyclonal Antibody Specific to the Mutated G-CSF Protein

Using the mutated G-CSF protein obtained from the recombinant *E. coli* in Example 5 as an antigen, a polyclonal antibody specific to the mutated G-CSF protein was prepared as follows. After emulsifying 400 µl of the purified mutated hG-CSF protein dissolved in a phosphate buffer in a concentration of 1 mg/ml with an equal volume of Freund's adjuvant (BRL), the emulsion was intramuscularly injected four times into rabbits (10 weeks old) in intervals of 11 days. 10 days after the fourth injection, blood was collected from the immunized rabbits by heart puncture. The collected blood was incubated at room temperature for 30 min, and then at 4° C. overnight for complete blood clotting. After centrifugation at 2,500 rpm for 30 min, the supernanat, that is, serum was obtained. Ammonium sulfate was added to the serum up to a final concentration of 40% to precipitate proteins. After dialyzing overnight in a 10 mM phosphate buffer (pH 7.0), antibody was purified using a DEAE Affi-Gel Blue gel (Bio-Rad Inc.) (Smith, C. P., Jensen, D., Allen, T. and Kreger, M. (Eds.) Information Resources for Adjuvants and Antibody Production. U. S. Dept. of Agriculture, 1997; and Hanly W. C. et al., ILAR Journal 37:93-118, 1995).

Example 7

Preparation of a Monoclonal Antibody Specific to the Mutated G-CSF Protein

After emulsifying 100 µd of the purified mutated hG-CSF protein (1 mg/ml) with an equal volume of Freund's adjuvant (BRL), the resulting emulsion was intraperitoneally injected three times into BALB/c mice (6-8 weeks old) in intervals of 2 weeks. After the third injection, an anti-mutant G-CSF protein antibody was found to be produced. After another 2 weeks, the mice were boosted with 100 µg of the purified mutated hG-CSF protein. 3 days after the boosting, splenocytes were obtained from the immunized mice, and mixed with SP2/0-Ag14 myeloma cells at a ratio of 10:1, and fusion was induced by adding a 50% polyethyleneglycol 1500 solution to the cell mixture, followed by incubation for 3 min. After centrifugation at 1,200 rpm for 8 min, the cell pellet was suspended in a HAT RPMI-1640 medium containing 10% fetal calf serum (FCS) at a density of $3.5\times10^6$ cells/ml. 0.1 ml of the cell suspension was then put into each well of a 96-well plate, and incubated in a 5% $CO_2$ incubator at 37° C. After 3 days, 0.1 ml of the HAT RPMI-1640 medium containing 10% FCS was added to each well of the plate, and half of the medium was replaced with a new medium every fourth day (Amyx, H. L., JAVMA 191:1287-1289, 1987; Akerstrom, B. et al., J Immunol 135:2589-2592, 1985; and Anon, Vet Health Inspectorate 6 pp. Rijswijk, The Netherlands, 1989).

After selective culturing in the HAT medium, the fused cells were screened for production of an anti-mutant G-CSF protein antibody by ELISA, as follows. First, the mutated hG-CSF protein used in the immunization of mice was diluted in 0.01 M carbonate-bicarbonate buffer (pH 9.6) in a concentration of 0.1 µg/ml, and 50 µl of the resulting dilution was added to each well of the plate, followed by incubation at 4° C. overnight to allow binding of the protein to the bottom of each well. The plate was washed four times with PBST (phosphate buffer saline, 137 mM NaCl, 2.7 mM KCl, 10 mM $Na_2HPO_4$, 2 mM $KH_2PO_4$, 0.15% Tween 20), and blocked with albumin by incubation at 37° C. for 30 min. Thereafter, 50 µl of the cell culture supernants was added to each well, and the plate was incubated at room temperature for 2 hrs, followed by washing four times with PBST. After diluting a biotin-conjugated anti-mouse immunoglobulin antibody, as a secondary antibody, in 0.1% BSA-PBST in a concentration of 1 µg/ml, 50 µl of the dilution was added to each well, followed at 37° C. for 1 hr. After washing four times with PBST, 50 µl of a 1:1000 dilution of streptavidin-horseradish peroxidase in 0.1% BSA-PBST was added to each well, and incubated at 37° C. for 30 min, followed by washing four times with PBST. 50 µl of a tetra-methylbenzidine (TMB) solution was added to each well, and incubated at room temperature, where the TMB was used as a substrate for peroxidase. After terminating the reaction with 2N sulfate, optical density was measured at 450 nm using an ELISA reader. Cells obtained from ELISA-positive wells were subcloned three times by limiting dilutions, in which the cells were diluted to 0.3 cell per well, to obtain hydridoma cells producing an anti-mutant hG-CSF protein monoclonal antibody. An anti-mutant hG-CSF protein monoclonal antibody was obtained from the stable hybridoma cells (Amyx, H. L., JAVMA 191:1287-1289, 1987; Akerstom, B. et al., J Immunol 135:2589-2592, 1985; and Anon, Vet Health Inspectorate 6 pp. Rijswijk, The Netherlands, 1989).

Example 8

Detection of Mutated G-CSF Protein Levels by ELISA

After being diluted in 0.01 M carbonate-bicarbonate buffer (pH 9.6), the anti-rabbit and anti-mouse mutated hG-CSF protein antibodies were added to each well of plates, along with ceruloplasmin, and the plates were incubated at 4° C. overnight to allow attachment of the antibodies to the bottom of each well. After being washed twice with PBST (0.15% Tween 20), the plates were blocked with 0.1% albumin at 37° C. for 1 hr. After washing twice with PBST, 50 µl of standard diluent buffer and each of specimens from normal individuals and cancer patients were added to the plates and carefully mixed, and the plates was incubated at 37° C. for 2 hrs, followed by washing four times with PBST. After being diluted in 10 mM phosphate buffer containing 0.15 M NaCl, 2.5 µg of peroxidase conjugated anti-human immunoglobulin antibody as a secondary antibody was added to each well, and the plates were incubated at room temperature for 30 min, followed by washing four times with PBST. 50 µl of a tetra-methylbenzidine (TMB) solution was added to each well, and incubated at room temperature under a dark condition, where the TMB was used as a substrate for peroxidase. After terminating the reaction with 2.5N sulfate, optical density was measured at 450 nm using an ELISA reader.

Figure 11:
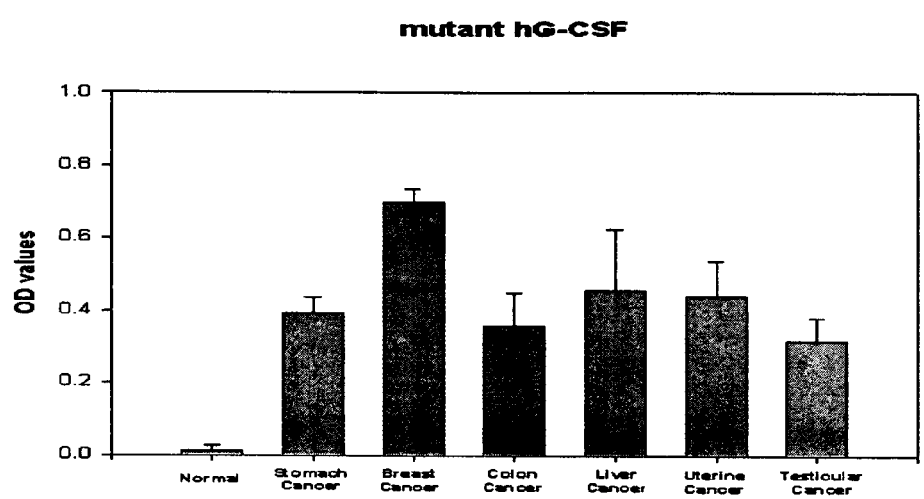
FIG. 11 is a graph showing levels of a mutated G-CSF protein having a deletion of an amino acid sequence corresponding to the exon 3 region in normal humans and cancer patients, which are measured using an antibody to the mutated G-CSF protein.

As shown in FIG. 11, mutated hG-CSF protein levels were found to be much higher in cancer patients than that in normal individuals. When comparing mutated hG-CSF protein levels of cancer patients to each other, breast cancer patients showed the highest level of the mutated hG-CSF protein.

As exemplified in detail in the above Examples, diagnosis of cancer may be easily performed by detecting deletion of exon 3 of G-CSF by PCR or using DNA chips, or by detecting a mutated G-CSF protein by ELISA. The conventional cancer biomarkers are unable to detect all kinds of cancer, as follows. The known cancer biomarkers having low organ specificity, such as CEA, BFP, TPA and IAP, have low sensitivity, thus generating false positive data. Also, the biomarkers having high organs specificity, which are exemplified as AFP, PIVKA II, Esterase I, CA19-9, CA50, Span-1 antigen, CA15-3 and BCA 225, are useful only for target organs. The diagnostic cancer marker based on deletion of the exon 3 region of G-CSF, discovered by the present inventors, may be used to easily diagnose cancer by immunochemical methods and molecular methods. Development and use of such a cancer marker may facilitate early discovery of cancer, thus largely contributing to effective treatment of cancer.

INDUSTRIAL APPLICABILITY

As described hereinbefore, the present invention provides a method of diagnosing cancer based on detection of deletion of the exon 3 region of G-CSF gene. The method of diagnosing cancer may be applied for diagnosis of a broad range of cancers, not only a specific cancer, and has effectiveness in easily diagnosing cancer by molecular methods, such as PCR, hybridization or use of DNA chips, or relatively simple immunochemical assays such as ELISA. In addition, a DNA chip for detection of deletion of the exon 3 region of G-CSF is advantageous in terms of enabling diagnosis of all kinds of cancer, in a simpler, quicker and more accurate manner than the conventional methods for diagnosis of cancer, and dealing with a large number of clinical specimens at one time, thereby leading to development and advance of human medicine and improvement of the public good, as well as largely contributing to development of DNA-chip technologies.

In addition, the mutated G-CSF protein having a deletion of an amino acid sequence corresponding to the exon 3 region, and an antibody to the mutated G-CSF protein, invented by the present inventors, may facilitate distinction of normal individuals and cancer patients. This fact indicates that detection of only G-CSF mutants allows accurate diagnosis of cancer and application of a large number of clinical specimens, thus largely contributing to development of protein-chip technologies.

The invention claimed is:

1. A microarray comprising a surface and a probe with
   i) nucleotide residues 106-213 of SEQ ID NO:7; or
   ii) one nucleotide sequence selected from the group consisting of SEQ ID NO:14, 15, 16 and 17; or
   iii) a fragment of the nucleic acid of residues 106-213 of SEQ ID NO:7 capable of binding to exon 3 of the nucleic acid encoding G-CSF, wherein said probe is immobilized on the surface of said microarray, wherein said microarray further comprises a control probe immobilized on said surface, wherein the control probe sequence consists of a nucleotide sequence selected from the group consisting of the nucleotide sequences of SEQ ID NO:10, 12, 13, 18, 19 and 20.

2. The microarray according to claim 1, wherein the probe comprises nucleotide residues 106-213 of SEQ ID NO:7.

3. The microarray according to claim 1, wherein the probe is selected from the group consisting of the nucleotide sequences of SEQ ID NO:14, 15, 16 and 17.

4. The microarray according to claim 1, wherein the surface of the microarray is glass.

* * * * *